United States Patent [19]
Fine

[11] Patent Number: 5,417,689
[45] Date of Patent: May 23, 1995

[54] THERMAL BALLOON CATHETER AND METHOD

[75] Inventor: Michael J. Fine, Coral Springs, Fla.

[73] Assignee: Cordis Corporation, Miami Lakes, Fla.

[21] Appl. No.: 182,776

[22] Filed: Jan. 18, 1994

[51] Int. Cl.⁶ .................... A61B 17/36; A61M 29/02
[52] U.S. Cl. ........................ 606/41; 606/194
[58] Field of Search ............... 606/27, 28, 191, 194, 606/192, 7; 604/96

[56] References Cited

U.S. PATENT DOCUMENTS

| | | |
|---|---|---|
| 4,709,698 | 12/1987 | Johnston et al. |
| 4,754,752 | 7/1988 | Ginsburg et al. ............... 606/27 |
| 4,779,479 | 1/1989 | Spears . |
| 4,955,377 | 9/1990 | Lennox et al. ............... 606/27 |
| 4,998,933 | 3/1991 | Eggers et al. |
| 5,019,075 | 5/1991 | Spears et al. ............... 606/28 |
| 5,035,694 | 7/1991 | Kaspryzk et al. |
| 5,092,841 | 3/1992 | Spears . |
| 5,114,423 | 5/1992 | Kasprzyk et al. ............... 606/191 |
| 5,151,100 | 9/1992 | Abele et al. ............... 606/28 |
| 5,190,540 | 3/1993 | Lee ............... 606/28 |
| 5,191,883 | 3/1993 | Lennox et al. ............... 606/27 |
| 5,226,430 | 7/1993 | Spears et al. |
| 5,292,321 | 3/1994 | Lee . |

FOREIGN PATENT DOCUMENTS 9103207  3/1991  WIPO .

*Primary Examiner*—Stephen C. Pellegrino
*Assistant Examiner*—William Lewis
*Attorney, Agent, or Firm*—Watts, Hoffmann, Fisher & Heinke

[57] ABSTRACT

The method and apparatus of the present invention is for treating a blood vessel stenosis region in a subject. The method comprises the steps of inserting a catheter into a subject until a balloon located at a distal end portion of the catheter is within a treatment region of a blood vessel. The catheter comprises an elongated tubular body member having first and second axially extending passages. The balloon is located at a distal end portion of the tubular body member and is in fluid communication with the first and second passages. A mechanism supplies fluid under pressure through the first passage to a first axial end portion of the balloon to inflate the balloon. A heater located within the balloon elevates the temperature of the fluid to a first temperature. The first temperature is maintained for a predetermined time interal. A thermocouple senses the temperature of the fluid within the balloon. A control establishes the temperature during a thermal treatment cycle in response to the temperature of the fluid sensed by the thermocouple. The second passage conducts the heated fluid from the balloon at a second axially opposite end portion of the balloon after the thermal treatment cycle. The heated fluid removed from the balloon is replaced with a fluid at a second temperature less than the first temperature through the first passage.

16 Claims, 2 Drawing Sheets

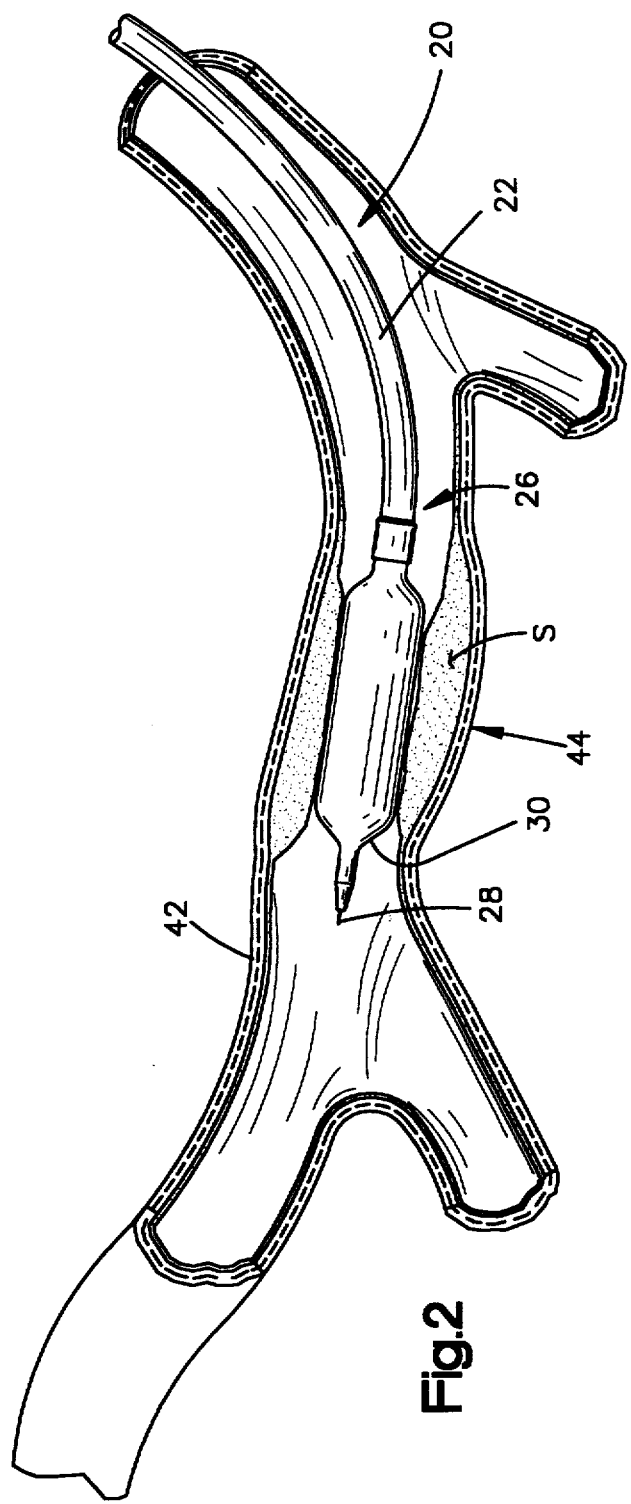
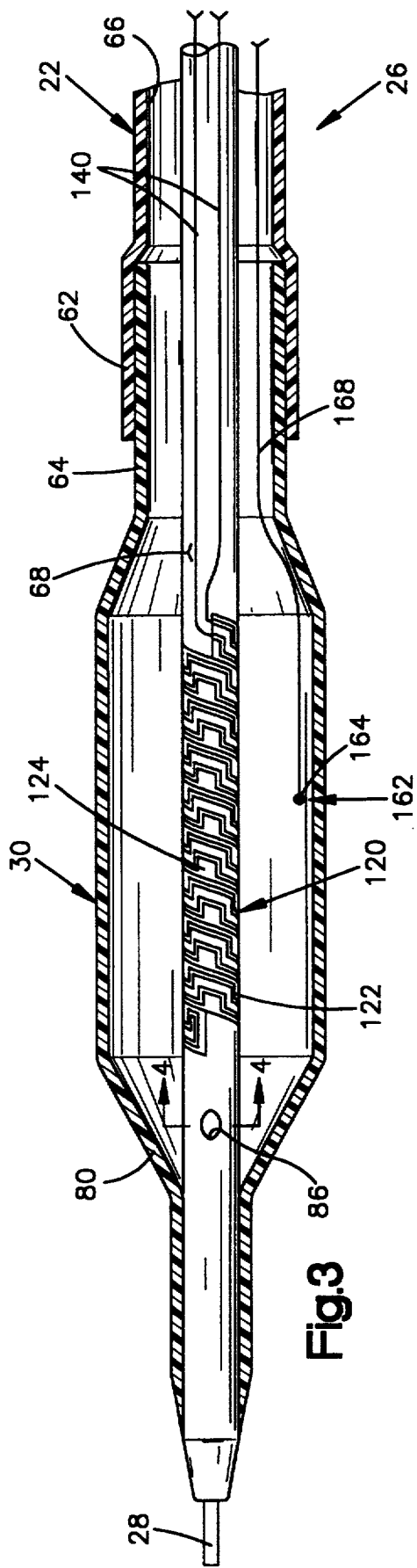

THERMAL BALLOON CATHETER AND METHOD

BACKGROUND OF THE INVENTION

1. Technical Field

The present invention relates generally to balloon angioplasty. In particular, the present invention relates to an improved catheter apparatus and method for thermal balloon angioplasty treatment of a blood vessel stenosis.

2. Description of the Prior Art

It is known that restricted blood flow through a blood vessel stenosis is treatable by balloon angioplasty. However, it is also known that after such balloon angioplasty treatment certain undesirable conditions, such as abrupt reclosure or restenosis, can occur. Improvements to balloon angioplasty and blood vessel stenosis treatment are disclosed in U.S. Pat. Nos. 4,799,479 and 5,190,540 in order to minimize the occurrence of the undesirable conditions of reclosure and restenosis.

U.S. Pat. No. 4,799,479 discloses inflating a balloon in a blood vessel treatment region against a stenosis. During the time that the balloon is inflated to expand and open the stenosis, heat is applied to the fluid which has inflated the balloon. The fractured stenosis plaque and the blood vessel expanded tissue which result from inflation of the balloon are elevated in temperature to fuse together the fragmented segments of the stenosis and to treat the expanded tissue. This elevation in temperature also coagulates any blood trapped between the fragmented segments or between the fragmented segments of the stenosis and the expanded tissue of the blood vessel created by the expansion and deformation of the treatment region of the blood vessel. The heating of the balloon inflating fluid is performed after the balloon is inflated and takes some amount of time.

U.S. Pat. No. 5,190,540 discloses an improved apparatus and method for thermal balloon angioplasty. The apparatus includes a balloon attached to a distal end of a catheter body. The catheter body has two fluid passages extending therethrough. One passage directs fluid into the balloon and the other passage directs fluid away from the balloon. Each passage has an opening communicating with one end of the balloon.

The method disclosed in the '540 patent includes heating the balloon inflating fluid prior to balloon inflation. This causes the fatty or lipid tissue in the stenosis treatment region of the blood vessel to liquify and become relatively pliable. Thus, as the balloon is inflated any fractures to the stenosis plaque and any fissures or mechanical trauma to the blood vessel wall are minimized due to the relatively pliable condition of the stenosis and surrounding tissue in the treatment region of the blood vessel. After the heated and inflated balloon is maintained in contact with the treatment region for a predetermined time interval, the fluid inflating the balloon is cooled.

The cooling is accomplished while the balloon is inflated by displacing the heated fluid in the balloon with a fluid at a relatively lower temperature. The cooling action of the balloon re-establishes the solid form of the tissue located in the treatment region of the blood vessel. Injecting cool fluid into the balloon causes the heat softened and pliable tissue to congeal in the shape of the inflated balloon. This minimizes tissue elastic recoil and tissue thermal injury which may cause abrupt vessel closure and restenosis. Heat is applied for only a short term and the blood vessel is remolded to increase the likelihood it remains opened.

It is desirable to minimize the total treatment time that the balloon is inflated to avoid long periods of little or no blood flow. However, the heat treatment and the cooling treatment time intervals are relatively fixed. It is important to minimize the transition time between a heat treatment cycle and/or cooling treatment cycle.

SUMMARY OF THE INVENTION

The present invention is directed to an improved thermal balloon catheter apparatus and method for angioplasty treatment of a blood vessel stenosis. The improvement provides an advantage over known thermal balloon catheters and methods because of a relatively quick and effective transition between heat and cooling treatment cycles of the angioplasty. The relatively quick transition minimizes the total time that the balloon must be inflated. The present invention also provides an improved heater for the balloon inflating fluid and an improved power supply and control for the heater.

The method of the present invention is for treating a blood vessel stenosis in a subject. The method comprises the steps of inserting a catheter into a subject until a catheter balloon is within a treatment region of a blood vessel. Fluid is found into the balloon at a first end portion of the balloon until the balloon contacts an inner wall of the treatment region of the blood vessel. The treatment region of the blood vessel is expanded by the balloon to increase the blood vessel's diameter. The fluid within the balloon is heated for a predetermined time interval while maintaining the balloon in contact with the treatment region of the blood vessel to soften the treatment region. After this heat treatment, the heated fluid is removed from the balloon through a return passage located at a second end portion of the balloon axially opposite the first end portion. The heated fluid is replaced with a cooler fluid at the balloon's opposite end to cool the treatment region of the blood vessel.

The inflating fluid within the balloon is cooled from a temperature of 60° C. or greater to under 38° C. in five seconds or less. The method further includes the step of providing a dual passage catheter body. The inflating step includes forcing the fluid through a first passage to the first end portion of the balloon. The heated fluid removing step includes venting the fluid from an opposite end of the balloon through a second passage.

The step of heating the fluid includes the step of energizing a current-carrying electrode which extends centrally between the first and second end portions of the balloon. The method further includes the step of monitoring the temperature of the fluid within the balloon during the heating step to control the supply of energy to the electrode. The method of the energizing step further includes energizing the electrode from a D.C. power supply.

The apparatus of the present invention is directed to an improved thermal balloon catheter structure. The catheter comprises an elongated tubular body member having first and second axially extending passages. A balloon is located at a distal end portion of the tubular body member and is in fluid communication with the first and second passages. A mechanism supplies fluid under pressure through the first passage to a first axial end portion of the balloon to inflate the balloon. A heater located within the balloon elevates the temperature of the fluid to a first temperature. A thermocouple senses the temperature of the fluid within the balloon. A control circuit establishes the temperature during a thermal treatment cycle in response to the temperature of the fluid sensed by the thermocouple. The second passage conducts the heated fluid from the balloon at a second axially opposite end portion of the balloon after the thermal treatment cycle. The heated fluid removed from the balloon is replaced with a fluid at a second temperature less than the first temperature through the first passage.

The catheter includes a valve that opens in response to pressure within the second passage increasing to a predetermined pressure to allow heated fluid within the balloon to enter the second exit passage, while maintaining a desired fluid pressure within the balloon. The tubular body member defines at least one of the first and second passages. The heater comprises an electrode supported by a second tubular member at a location within the balloon and electric leads extending through one of the first and second passages to an external energy source. A strip of material encapsulates the electrode to electrically insulate the electrode from the inflating fluid located within the balloon. The catheter electrode is helically wound around a portion of the second tubular member.

BRIEF DESCRIPTION OF THE DRAWINGS

Further features of the present invention will become apparent to those skilled in the art to which the present invention relates from reading the following specification with reference to the accompanying drawings, in which:

FIG. 2 is an enlarged view of an end portion of the catheter in FIG. 1 inserted into a blood vessel, and illustrated with a balloon inflated against a stenosis;

FIG. 3 is a longitudinal cross-sectional view of the inflated balloon located at the end portion of the catheter in FIG. 2.

DESCRIPTION OF A PREFERRED EMBODIMENT

Figure 1:
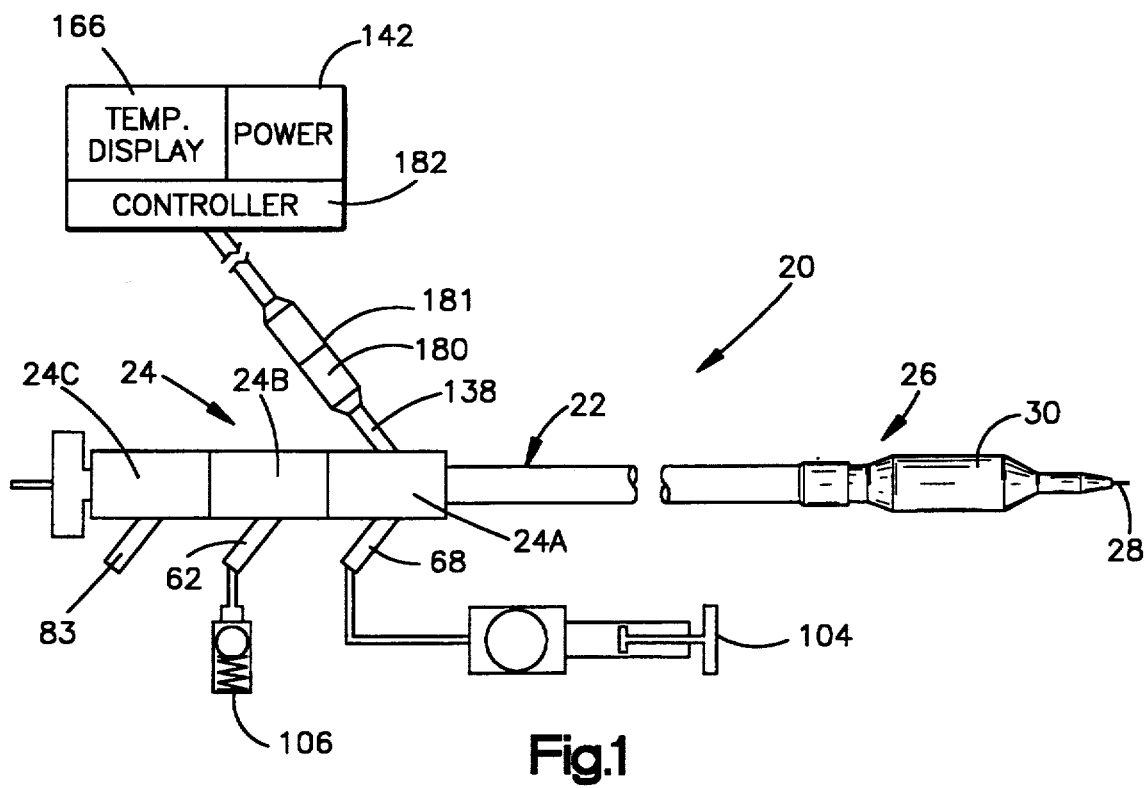
FIG. 1 is a schematic view of an improved thermal balloon catheter embodying the present invention.

An improved thermal balloon catheter 20 is illustrated in FIG. 1. The catheter 20 is intended for use in the heat treatment of a blood vessel having a stenosis S (FIG. 2) and the cooling treatment of the repaired portion of the blood vessel. The catheter 20 includes an elongated tubular body 22 with a proximal end portion 24 and a distal end portion 26. The proximal end portion 24 remains outside of the blood vessel of a subject and is manipulated to control various functions of the catheter 20 and the length of insertion of the distal end portion 26 into a blood vessel into the subject. The proximal end portion of the catheter 20 includes a luer fitting (not shown) that mates with a plurality of in-line side port adapters 24A, 24B, 24C whose functions are described below. The distal end portion 26 of the catheter 20 supports an inflatable balloon 30.

A guidewire 28 extends from the proximal end portion 24 to just beyond the balloon's distal end. The guidewire 28 may move axially with or relative to the tubular body 22. A distal end of the guidewire 28 is small enough to fit through very small openings that exist in the stenosis S.

As illustrated in FIG. 2, the blood vessel 42 includes a stenosis S which totally or partially closes the blood vessel and restricts blood flow. The stenosis S is typically comprised of a plaque-like material with fatty or lipid pockets. The size of the stenosis S gradually increases over time by the plaque-like material gradually collecting radially inward of the blood vessel to block or at least restrict blood flow through the blood vessel 42. The distal end portion 26 of the catheter 20 has been inserted into a blood vessel 42 of a subject. The guidewire 28 is pushed through the stenosis S and the balloon 30 is then moved over the guidewire until it bridges the stenosis S in the blood vessel 42.

The balloon 30 is inflated into engagement with the stenosis S to expand the stenosis and increase the lumen diameter of the blood vessel 42 to increase blood flow. The improved thermal balloon catheter 20 and method, embodying the present invention, minimizes the fracturing and fissuring of the plaque-like deposits of the stenosis S, remolds the treatment region 44 and minimizes thermal injury to the blood vessel 42.

The distal end portion 26 of the catheter 20 is illustrated in detail in FIG. 3. The tubular body 22 is strong enough to resist collapsing in a direction normal to the guidewire 28, yet flexible enough to bend. The balloon 30 is fixed at one axial end to an outer tubular member 62 of the tubular body 22. An end portion of the outer tubular member 62 engages and seals around the entire periphery of a first axial end portion 64 of the balloon 30. The outer tube 62 defines a first fluid passage 66 into which pressurized fluid is communicated to the first axial end portion 64 of the balloon 30 to inflate the balloon.

The tubular body 22 of the catheter 20 also includes an elongated inner tubular member 68 which is strong enough to resist collapsing in a direction normal to the guidewire 28, yet flexible enough to bend. The inner tubular member 68 extends substantially coaxially within the passage 66 defined by the outer tubular member 62. The inner tubular member 68 extends axially beyond the end of the outer tubular member 62. The inner tubular member 68 is also connected to the balloon 30 at a second axial end portion 80 of the balloon opposite the first axial end portion 64. The second axial end portion 80 of the balloon 30 provides a fluid tight seal around the entire periphery of an end portion of the inner tubular member 68.

Figure 4:
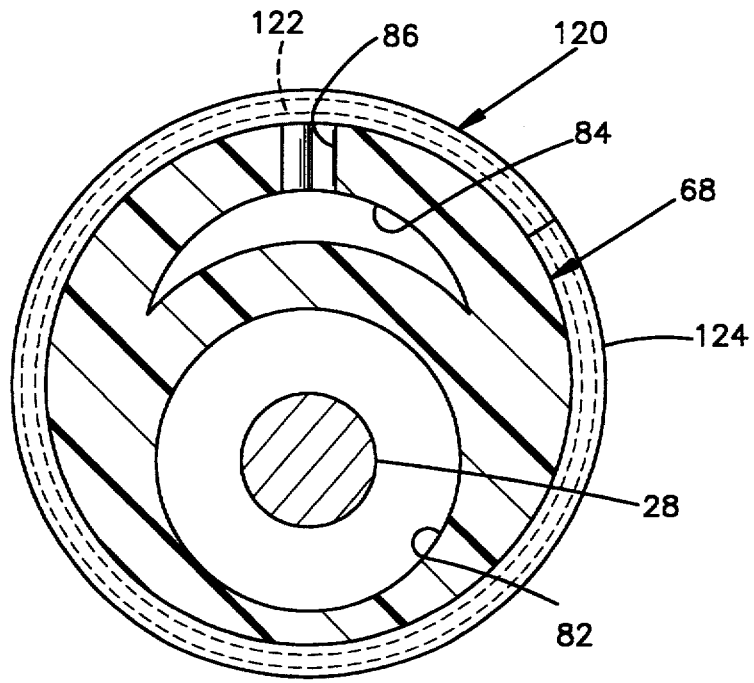
FIG. 4 is a cross-sectional view of a portion of the catheter in FIG. 3, taken approximately along line 4—4 in FIG. 3.

The inner tubular member 68 defines two passages 82, 84 (FIG. 4) extending substantially the entire length of the inner tubular member. One passage 82 is circular in cross-section taken normal to the extent of the inner tubular member 68 and allows the metal guidewire 28 to extend therethrough. The passage 82 also permits certain fluids or medicaments and the like to be injected into the blood vessel 42 downstream of the balloon 30 through an infusion port 83 in the proximal adapter 24C. The other passage 84 is crescent-shaped in cross-section and is in fluid communication with the interior of the balloon 30 at a distal end 80 of the balloon through an opening 86.

As fluid under pressure is communicated through the first passage 66 in the outer tubular member 62 into the first axial end portion 64 of the balloon 30, the balloon inflates and expands radially outwardly towards the blood vessel 42. The balloon 30 is further inflated against the inner surface of the stenosis S by conducting more fluid under pressure into the balloon. Fluid also enters the opening 86 in the inner tubular member 68 and fills the passage 84. The balloon 30 treats the stenosis S by expanding it radially outwardly to increase its cross-sectional area.

A heater 120 extends along the outside of a portion of the tubular member 68 and within the balloon 30. Fluid communicated through the passage 66 to the balloon interior is heated to an elevated temperature rapidly due to the relatively large surface area of the heater 120. The fluid within the balloon 30 may be heated prior to inflation of the balloon, concurrent with inflation or after the balloon is inflated. Preferably, heating takes place prior to and concurrent with inflation of the balloon 30 to minimize the time that the balloon is inflated and restricting blood flow.

The heater 120 comprises a resistive heating element or electrode 122 (FIGS. 3 and 4) which is electrically insulated from the fluid within the balloon 30. The electrode 122 is formed in a repeating right angle zig-zag pattern for the length of the heater 120. The pattern enables a relatively large amount of resistive element surface to be located within a given linear dimension of the heater 120. The electrical insulation feature is provided because the electrode 122 is embedded and encapsulated in a strip 124 of electrically non-conductive material. The heater 120 is located within the balloon 40 by winding the strip 124 in a helical arrangement at a 45° angle along a portion of the inner tubular member 68 located in the balloon 30. The heater 120 is preferably centered axially within the cylindrical portion of the balloon 30. The helical configuration of the heater 120 allows the portion of the inner tubular member 68 to which the heater is mounted to remain flexible. Thus, the heater 120 is not only electrically insulated but retained in a fairly constant cylindrical configuration about the inner tubular member 68 within almost the entire axial extent of the balloon 30. The heater 120, is in contact with the inflating fluid located within the balloon 30, so heating can occur quickly when the electrode 122 is energized.

Heating the inflating fluid within the balloon 30 while, and as, the balloon is inflated liquifies the fatty or lipid material in and around the stenosis S to minimize injury to the treatment region 44 upon expansion of treatment region. The heat or thermal treatment cycle is maintained for a predetermined time interval while the balloon 30 is inflated against the stenosis S. The heated inflation fluid in the balloon 30 is then forced out of the balloon and replaced with relatively cooler fluid while the balloon remains inflated to cool the balloon and reshape the treatment region 44 of the blood vessel 42. The cooling cycle permanently sets the treatment region 44 in the reshaped form to prevent reclosure and restenosis and minimizes thermal injury to the blood vessel 42. Cooling solidifies the fatty or lipid material in the expanded stenosis S when the balloon 30 is still inflated to remold the treatment region 44 to have the largest flow area possible.

By way of example, typically during a thermal balloon treatment, the balloon 30 is inflated against the stenosis S and heated to a temperature of at least about 60° C. (140° F.). The fluid in the balloon 30 may be heated prior to inflation of the balloon 30, concurrent with inflation of the balloon or after the balloon is inflated as long as there is some fluid in the balloon when heating starts. The time interval for engaging the stenosis S during a heat treatment cycle while maintaining the stenosis S open is a predetermined time, for example at least ten to one hundred twenty seconds. After a heat treatment cycle, the balloon 30 is cooled to under 38° C. (93° F.) in five second or less and held for approximately ten to thirty seconds. The balloon 30 is then deflated to permit blood to flow through the blood vessel 42. The cooling treatment cycle minimizes thermal injury to the treatment region 44 of the blood vessel. The thermal angioplasty treatment cycle may be repeated or performed more than once in a treatment region 44 of the blood vessel 42 to maximize the effectiveness of the treatment.

The fluid inflating the balloon 30 is heated to about 60° C. (140° F.) and maintained for at least fifteen to thirty seconds for the thermal treatment cycle time interval. The inflation fluid is quickly cooled to under 38° C. (93° F.) with a relatively constant cooling rate in approximately five seconds or less for the transition cycle. The relatively fast transition time between the thermal and cooling treatment cycles is enabled by the structure of the catheter 20 embodying the present invention. The time interval that the cooling treatment cycle is maintained is about equal to the time interval of the thermal treatment cycle. The inflating fluid can also be cooled to about 20° C. for the cooling treatment cycle but will likely take longer than the five seconds required to get to 38° (93° F.).

Fluid in the passage 66 defined by the outer tubular member 62 is introduced through the port 68 by an inflation device 104 (FIG. 1). The inflation device 104 may be as simple as a syringe in fluid communication with the fluid passage 66. Upon axial movement of a member, such as a piston, in the inflation device 104 the fluid within the passage 66 and in the balloon 30 is increased in pressure. A slight rise in fluid pressure will inflate the balloon 30 if it is unrestricted. It will be apparent that the balloon will require more fluid pressure, such as two atmospheres or more, if it is restricted by a relatively large stenosis S.

The fluid within the passage 84 also is subject to the same pressure as the fluid in the balloon 30 and the passage 66. When the fluid pressure in the passage 84 reaches a level more than approximately two to five atmospheres, for example, an adjustable pressure dependent vent valve 106 coupled to the adapter 24B by a side port 62 opens to permit fluid flow through the passage 84. The parameters are set by the attending physician as a function of the patient's needs and conditions. Thus, the fluid from the inflation device 104 which is considerably cooler than the heated fluid within the balloon 30 enters the balloon while heated fluid flows from the balloon. This flow cools the heater 120, the balloon 30 and the treatment region 44 of the blood vessel 42.

The fluid flow across the heater 120 from a first axial end portion 64 of the balloon 30 to a region near the second axial end portion 68 of the balloon is particularly advantageous. Such flow assures that a relatively large percentage of the heated fluid within the balloon 30 is replaced with the relatively cooler fluid from the inflation device 104 entering through the passage 66. Thus, if the majority of the fluid within the balloon 30 is at an elevated temperature, that heated fluid flows from the balloon through the opening 86 and into the passage 84 to be expelled. The heated inflating fluid is replaced with a fluid at a relatively lower temperature to cool the balloon 30 and the treatment region 44 in the blood vessel 42.

A significant advantage is that this removal of heated fluid is positive and cooling occurs relatively quickly and at a relatively constant and predictable rate. Thus, the transition cycle is done relatively quickly as the balloon 30 is inflated against a treatment region 44 of the blood vessel 42. The positive and relatively constant cooling rate during the transition cycle assures that the treatment region 44 is not shocked by a too rapid of cooling while assuring that cooling fluid flow does take place. The cooling treatment cycle also takes place relatively quickly and, therefore, periods of reduced blood flow are minimized.

The electrode 122 is energized by electronically insulated wires 140 extending through the passageway 66 and out a side port 138 for coupling to an external power source 142. The power source 142 is preferably a D.C. battery or a series of D.C. batteries. The D.C. power supply provides advantages because it is easier to implement to a greater degree than other power supplies, such as A.C., laser or radio frequency power supplies. The D.C. power supply has significant advantages over an A.C. power supply because it can be battery powered.

A temperature sensor 162 (FIG. 1) is also provided. The temperature sensor includes a thermocouple 164 (FIG. 3) located within the axial extent of the balloon 30 at a location such as at the midpoint of the heater 120. The thermocouple 164 is electrically connected with a visual display 166 by an electronically insulated wire 168 extending through the tubular body 22. The wires 140, 168 terminate at a connector 180 which mates with a connector 181 for connecting the power supply and display 166 to the catheter 20.

The temperature of the fluid within the balloon 30 can be sensed by the thermocouple 164 and communicated to the display 166. A temperature signal is also communicated to a controller 182. The controller 182 controls the application of power to the heater 120 in the balloon 30. The controller 182 maintains the desired temperature for a specified time interval by monitoring the sensed temperature within the balloon 30 and adjusting energization of the electrode 122. The controller 182 may include a microprocessor and clock that are programmed to control the power supply in response to, or as a function of, the temperature sensed within the balloon 30 or in response to the time that the balloon inflating fluid is at a certain temperature. The parameters are set by an attending physician depending on the patient's needs and condition.

The heater 120 is fabricated from a flat 0.0005 inch thick ribbon ni-chrome wire arranged in the form of a zig-zag pattern and encapsulated within a printed circuit board insulating material strip having a thickness of 0.001 inch. Adhesive is applied to a side of the strip which will contact the tube 68. The printed circuit board strip is helically wound around an end portion of the tube 68 to form the heater 120. The heater 120 is held in place by a teflon sleeve (not shown) than slips over the tube 68 and heater 120. A liquid adhesive is then applied at opposite ends of the teflon sleeve. The adhesive wicks under the sleeve and bonds the heater 120 to the tube 68. Once the adhesive dries, the sleeve is removed and the wires 140 are attached to the electrode 122.

From the above description of a preferred embodiment of the invention, those skilled in the art will perceive improvements, changes and modifications. Such improvements, changes and modifications within the skill of the art are intended to be covered by the appended claims.

Having described at least one preferred embodiment of the invention, what is claimed is:

1. A method for treating a blood vessel stenosis in a subject, said method comprising the steps of:
   inserting a catheter into a blood vessel of a subject until a balloon located at a distal end portion of the catheter is within a stenosis treatment region of the blood vessel;
   conducting fluid under pressure into the balloon at a first end portion of the balloon to inflate the balloon to contact the inner surface of the treatment region of the blood vessel and expand the treatment region of the blood vessel to increase the flow area in the treatment region of the blood vessel;
   heating the fluid within the inflated balloon for a predetermined time interval while maintaining the balloon in contact with the treatment region of the blood vessel;
   exhausting the heated fluid from the balloon through a return passage located at a second end portion of the balloon axially opposite the first end portion of the balloon; and
   replacing the exhausted fluid with cooler fluid to cool the heated treatment region of the blood vessel by conducting the cooler fluid into the balloon at the first end portion of the balloon while maintaining the balloon inflated.

2. The method of claim 1 wherein said steps of exhausting and replacing the heated fluid includes the step of cooling the fluid within the balloon from a temperature of 60° C. or greater to a temperature of 38° C. or less in five seconds or less.

3. The method set forth in claim 2 wherein said rate of cooling is constant during said replacing step.

4. The method of claim 1 further including the step of providing a dual passage catheter body and wherein said inflating step includes forcing the fluid through a first passage to the first end portion of the balloon and wherein said exhausting step includes venting the heated inflating fluid from the second end portion of the balloon through a second passage.

5. The method of claim 1 where said step of heating the fluid includes the step of energizing a current-carrying electrode located within the axial extent of the balloon.

6. The method of claim 5 further including the step of sensing the temperature of the fluid within the balloon during said heating step and controlling the application of energy to the electrode as a function of the temperature sensed.

7. The method of claim 5 wherein said energizing step further includes energizing the electrode with D.C. power supplied by at least one battery.

8. The method of claim 5 further including the step of providing the electrode at a location within the axial extent of the balloon between the first and second end portions of the balloon.

9. The method set forth in claim 8 wherein said electrode providing step includes electrically insulating the electrode from contacting the inflating fluid within the balloon.

10. The method set forth in claim 1 wherein said heating step time interval is at least ten seconds.

11. The method set forth in claim 9 further including a holding step after said replacing step, said holding step comprises holding the balloon in an inflated condition for at least ten seconds.

12. An improved thermal balloon catheter for treating a blood vessel stenosis in a subject, said catheter comprising:
- an elongated catheter body having an outer longitudinally extending member spaced from an inner longitudinally extending tubular member by a fluid conveying gap;
- a balloon attached to a distal end portion of said catheter body in fluid communication with said fluid conveying gap and overlying a portion of the inner tubular member that extends beyond the outer member;
- a source for supplying fluid under pressure from a proximal end of the catheter body through said gap to inflate said balloon;
- a resistive heating electrode comprising a conductive strip which is helically wound onto a portion of said tubular member within the balloon for increasing the temperature of the fluid located within said balloon;
- a sensor located within the balloon for sensing the temperature of the fluid within said balloon; and
- a controller electrically coupled to the sensor and also electrically coupled to the heating electrode by conductors passing through the catheter body for energizing the electrode to control the temperature of fluid within the balloon during a thermal treatment interval in response to the temperature of the fluid within said balloon;
- said inner tubular member defining an opening into a passage that extends through at least a portion of the inner tubular member for removing heated fluid from the balloon, said opening located within a distal end portion of said balloon.

13. The catheter of claim 12 additionally Comprising a valve in fluid communication with said passage extending through the inner member that opens in response to pressure within said passage increasing to a predetermined pressure to allow fluid to flow through said passage and from said balloon.

14. The catheter of claim 12 wherein said catheter further includes electric leads extending through the gap to a proximal end of the catheter where the leads are connected to an external energy source.

15. The catheter of claim 14 further including a material encapsulating said resistive heating electrode to electrically insulate said resistive heating electrode from fluid located within said balloon.

16. The catheter of claim 14 wherein said external energy source comprises a D.C. energy source.

* * * * *